United States Patent [19]

Lonsdale et al.

[11] Patent Number: 4,948,506
[45] Date of Patent: Aug. 14, 1990

[54] PHYSICOCHEMICALLY FUNCTIONAL ULTRATHIN FILMS BY INTERFACIAL POLYMERIZATION

[75] Inventors: Harold K. Lonsdale; Walter C. Babcock; Dwayne T. Friensen; Kelly L. Smith; Bruce M. Johnson, all of Bend; Carl C. Wamser, West Linn, all of Oreg.

[73] Assignee: Bend Research, Inc., Bend, Oreg.

[21] Appl. No.: 272,213

[22] Filed: Nov. 14, 1988

Related U.S. Application Data

[63] Continuation-in-part of Ser. No. 883,043, Jul. 7, 1986, Pat. No. 4,784,736.

[51] Int. Cl.$^5$ .............................................. B01D 13/00
[52] U.S. Cl. ................................ 210/490; 210/500.37; 210/500.38; 210/500.41
[58] Field of Search ..................... 424/484; 435/176; 204/157.6; 210/490, 500.41, 500.37, 500.38

[56] References Cited

U.S. PATENT DOCUMENTS 4,431,428  2/1984  Schmer ........................ 424/484 X

*Primary Examiner*—Frank Spear
*Attorney, Agent, or Firm*—Chernoff, Vilhauer, McClung & Stenzel

[57] ABSTRACT

Interfacially-polymerized ultrathin films containing physicochemically functional groups are disclosed, both with and without supports. Various applications are disclsoed, including membrane electrodes, selective membranes and sorbents, biocompatible materials, targeted drug delivery, and narrow band optical absorbers.

36 Claims, 3 Drawing Sheets

PHYSICOCHEMICALLY FUNCTIONAL ULTRATHIN FILMS BY INTERFACIAL POLYMERIZATION

The government has rights in this invention under Department of Energy Contract No. DE-FG06-85ER13389.

This is a continuation-in-part of U.S. application Ser. No. 883,043, filed July 7, 1986, now U.S. Pat. No. 4,784,736.

BACKGROUND OF THE INVENTION

Over the past three decades, considerable emphasis has been placed on the development of very thin polymeric films. For the most part, these thin films have been used as membranes, to effect chemical separations. Such processes as reverse osmosis for water desalination, gas separations as used in the purification of natural gas and in the production of oxygen-enriched air, and pervaporation which is used to break commercially important azeotropes, all rely on the availability of very thin, highly selective membranes. These and other processes are described in Volume VII of the "Techniques of Chemistry" series entitled "Membranes in Separations" (1975) by Hwang and Kammermeyer. In all membrane separation processes, the transmembrane flux is a key criterion in determining the cost of the process. High flux is generally associated with thin membranes, in keeping with Fick's first law, and considerable research and development has been expended toward making very thin, yet still highly selective membranes. "Selectivity" refers to the ability of the membrane to pass one species in a mixture while retaining other species. High selectivity is essential to effecting clean separations. The first technical breakthrough was the reverse osmosis membrane invented by Loeb and Sourirajan and disclosed in U.S. Pat. No. 3,133,132. Numerous types of membranes have been made since then using the Loeb-Sourirajan technique. See, for example, Kesting, 50 *Pure & Appl. Chem.* 633 (1978), who discloses asymmetric (skinned) cellulosic membranes, and Broens et al., 32 *Desalination* 33 (1980), who disclose similar membranes of cellulose acetate, polysulfone, polyacrylonitrile, and polydimethylphenyleneoxide.

The second breakthrough in making thin, selective membranes was due primarily to Cadotte. Cadotte borrowed from the teachings of Morgan, who first described in detail "interfacial polymerization." Interfacial polymerization (IP) is a process in which a very thin film (or membrane) can be made by reacting two monomers at the interface between two immiscible solutions. It is best described by example. "Nylons" are a class of polymers referred to as polyamides. They are made, for example, by reacting a diacid chloride, such as adipoyl chloride, with a diamine, such as hexamethylene diamine. That reaction can be carried out homogeneously in a solution to produce the polymer in resin form. However, it can also be carried out at an interface by dissolving the diamine in water and floating a hexane solution of the diacid chloride on top of the water phase. The diamine reacts with the diacid chloride at the interface between these two immiscible solvents, forming a polyamide film at the interface which is rather impermeable to the reactants. Thus, once the film forms, the reaction slows down drastically, so that the film remains very thin. In fact, if the film is removed from the interface by mechanical means, fresh film forms at the interface, because the reactants are so highly reactive with one another.

Cadotte used such knowledge of interfacial polymerization techniques to produce extremely thin, supported films such as are disclosed in U.S. Pat. No. 4,277,344. As a modification of the two immiscible liquid phases, he dissolved one reactant in a solvent and then used that solution to fill the pores of a microporous substrate membrane. He then exposed that wet membrane to a second, immiscible solvent containing the other reactant. An interfacially polymerized, very thin film formed at the surface of the microporous substrate, which then served as a support for the very thin film. Numerous adaptations of the Cadotte technology have been made using essentially the same IP method.

Morgan, in Volume 20 of the "Polymer Reviews" series entitled "Condensation Polymers: By Interfacial and Solution Methods" (1965), describes numerous chemistries that can be used to make polymers interfacially. Among the important chemistries are: polyamides, as already described; polyureas, polyurethanes, polysulfonamides, and polyesters; several other less important classes are also described. Morgan and others have also described the factors important to making continuous, thin interfacial films: temperature, the nature of the solvents and co-solvents, the concentrations of the two reactants, and the reactivity of the two monomers. Id. at pages 486–509. Refinements of the art developed over the past 20 years include the use of "blocked" or protected monomers that can be later unblocked to alter the chemistry of the finished film, the use of posttreatment of the films to alter their chemistry, and the use of heteroatoms in the monomers to alter the properties of the final film or membrane. In the classical organic chemistry sense, these alterations would be referred to as changes in the chemical "functionality," i.e., changes in those groupings of atoms that cause a substance to enter into its characteristic chemical reactions with another substance.

SUMMARY OF THE INVENTION

According to the present invention there is provided a class of thin films with a different kind of "functionality" than the classic organic chemistry "functionality" referred to above. In the context of the present invention, "functionality" is defined to mean the state of being physicochemically, including photochemically and electrochemically, reactive. The term is not intended to include characteristic chemical reactivity owing to the presence of free "functional" groups in the classic organic chemistry sense, such as a vinyl group, a hydroxyl group or a carboxyl group. The thin films of the present invention are physicochemically functional in the sense of containing moieties capable of electron transfer, of chelation or complexation, of enzymatic activity, of photochemical activity, or of biological activity. It has been found that the IP method can be used to produce ultrathin (20 to 2000 nanometers thick) films that contain such functionality as an integral part of the polymeric film, such that the ultimate film retains the physicochemical functionality of the original monomeric moiety. The IP method of the present invention provides means for incorporation of that physicochemically functional monomeric moiety into the polymeric film without substantially altering its physicochemical functionality, thus endowing the film with that same physicochemical functionality. Thus, in a sense, the present invention may be regarded as a method of binding a physicochemically functional moiety within a thin polymeric matrix, while at the same time leaving that moiety available to enter into its characteristic physicochemical reaction(s).

Preparation of such ultrathin, physicochemically functional films is essentially a two-step process comprising the steps of:

(1) forming one or more polymerizable derivatives of a discrete monomeric or prepolymeric molecule possessing physicochemical functionality; and (2) forming by IP an ultrathin film of the derivative(s) of the molecule so as to imbue the film with substantially the same physicochemical functionality as possessed by the original monomeric or prepolymeric molecule.

In terms of a chemical reaction, the following representational scheme summarizes the method of the present invention:

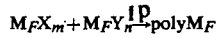

where $M_F$ is a monomeric or prepolymeric molecule or moiety with a given physicochemical functionality such as a photochemically or enzymatically active agent; X and Y are chemically functional groups in the classic organic chemistry sense, such as amines and acid chlorides, which have complementary reactivity (such as in a condensation reaction) allowing them to undergo IP; m and n are integers $\geq 2$; IP is an interfacial polymerization reaction; and poly$M_F$ is an interfacially-polymerized polymer containing discrete repeating units of the physicochemically functional moiety $M_F$.

The conversion of the original functional monomer, $M_F$, into the polymerizable monomeric derivatives, $M_F X_m$ or $M_F Y_n$, is carried out by standard synthetic techniques so as to retain the physicochemical functionality of $M_F$. The required synthetic techniques will necessarily be different for the various types of X and Y reactive groups which could be used and may also have to be modified to assure that the physicochemical functionality of $M_F$ is retained. Specific examples of the X and Y mutually reactive groups include amines and acid halides (to form polyamides), alcohols and acid halides (to form polyesters), thiols and acid halides (to form polythioesters), amines and isocyanates (to form polyureas), alcohols and isocyanates (to form polyurethanes), and amines and sulfonyl halides (to form polysulfonamides). Other lesser known but potentially useful examples of mutually reactive groups capable of entering into condensation reactions are set forth in Chapter 9 of Morgan, "Condensation Polymers: By Interfacial and Solution Methods" (1965).

DETAILED DESCRIPTION OF THE INVENTION

According to the present invention, ultrathin films containing physicochemical functionality as defined herein may be prepared by IP methods. The term "films" is meant to include films in the shape of flat sheets, tubes, hollow fibers, microcapsules, or beads. In most applications, because the thin films are physically too weak to be self-supporting, in use they would be applied as a coating on some physically robust substrate in one of the above-described shapes.

The IP method can be used to produce thin, functional films for use in a host of applications, including sensors in the form of membrane electrodes, membranes for selective separations utilizing crown ethers or other carriers, selective sorbents, biocompatible materials, targeted drug-delivery devices including membrane-bound antigens, and optical filters, as described in detail below.

MEMBRANE ELECTRODES

The method of the present invention may be used for the preparation of a class of sensors known as "membrane electrodes." The use of electrodes as sensors in analytical chemistry has been practiced since early in this century, with the introduction of the glass electrode for the determination of pH. Within the past two decades, a series of related electrodes has been developed, referred to as "ion-specific electrodes," (ISE) with which a wide variety of ions in solution—now numbering more than 20—can be quantitatively detected. See A. K. Covington (Ed.), *Ion-Selective Electrode Methodology*, Volumes I and II (1979).

Figure 1:
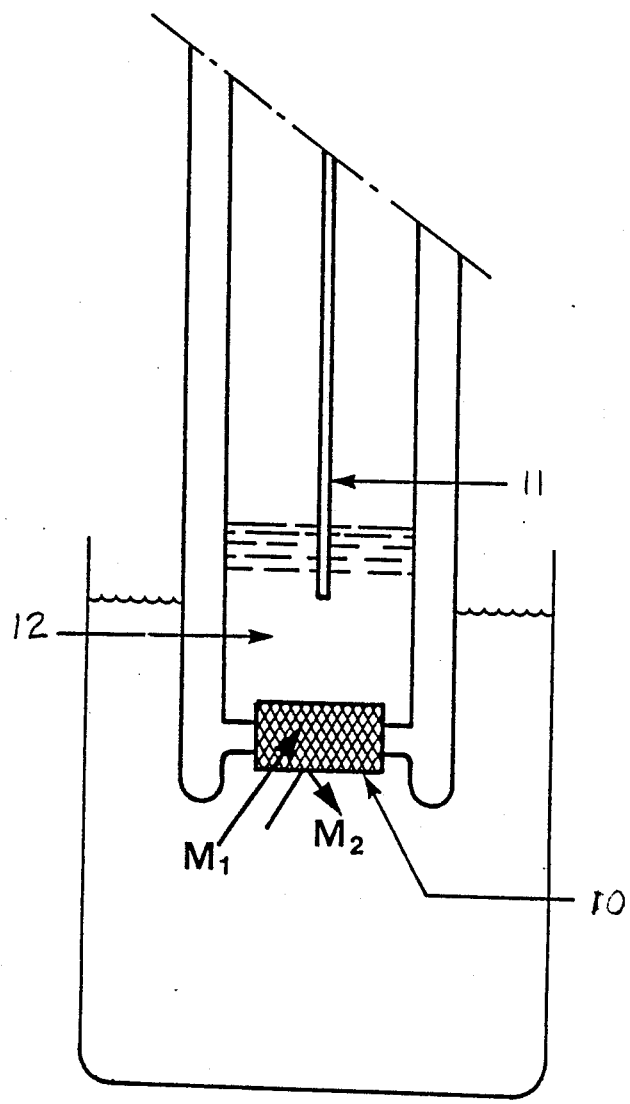
FIG. 1 is a schematic drawing of a conventional ion-specific electrode.

Some of these electrodes contain a semipermeable membrane in which a specific reversible reaction occurs involving the ion to be detected. That reaction causes a small but measurable electrical potential to be developed across the membrane, which is then measured and related to the metal-ion concentration in solution. A conventional membrane-containing ISE of this type is shown in FIG. 1, where $M_1$ is the ion to be detected. The membrane contains some chemical species that interacts, for example, by complexation, specifically with the metal ion to be detected; the concentration of that ion in solution may thus be determined even when other ionic species, denoted by $M_2$ in FIG. 1 and to which the chemical species is inert, are present. A reference electrode, which has a constant potential with respect to the test solution, measures the potential developed across the membrane. Electrical contact between the membrane and the reference electrode is made through the internal filling solution which contains a salt and thus conducts electric current.

Such membrane electrodes, however, are known to suffer from two deficiencies: they are unstable and they exhibit slow response times. They are unstable because the reactive species in the membrane can leach out with time, and because the composition of the internal filling solution can change with time because of ion migration from the test solution across the membrane. Perhaps the most serious error-generating problem common to most membrane ISEs is the so-called "liquid junction potential." The liquid junction potential arises from the fact that the cations and anions in the internal filling solution that carry current from the membrane element of the ISE to the reference electrode have different mobilities in the solution. The passage of current thus causes charge separation which results in a potential (the liquid junction potential) between the membrane element and the reference electrode. The liquid junction potential changes with temperature and it also changes with the composition of the internal filling solution.

Current ISEs exhibit slow response times due to the use of relatively thick and impermeable membranes as the sensor elements. These thick membranes require relatively long time periods for ions to diffuse into them, and they are therefore slow to reach equilibrium with the sample solution. When the membranes are made more permeable, for example by swelling them with a suitable plasticizing agent, their selectivity is reduced because the permeability of the membrane to all of the ionic species in the sample solution is increased.

The problems of membrane ISE instability and slow response can be solved by incorporating the sensor species having the desired physiochemical functionality into the membrane by means of IP. Very thin, fast-responding sensor elements for ISEs may be prepared by interfacial polymerization of a monomer that contains a physicochemically functional group that reacts with the ion of interest. The interfacially polymerized membrane can be formed directly on the reference electrode wire, thereby eliminating the need for an internal filling solution, with its inherent problem of a liquid junction potential. Such membrane ISEs would be stable because the functional groups are covalently bound within the membrane-sensing element and they therefore cannot leach out of the membrane over time. Other advantages of preparing membrane ISEs by directly coating the reference electrode with a physicochemically functional membrane as defined herein are that the electrode can be made extremely small and at low cost.

Many types of chelating compounds can be used to prepare membrane ISEs. As noted by Frensdorff in 93 JACS 600 (1971), suitable reactive groups for the preparation of membrane ISEs sensitive to alkali and alkaline earth ions (such as $Na^+$, $K^+$, $Ca^{++}$, and $Mg^{++}$) include amine and acid chloride derivatives of crown ethers such as 15-crown-5 (I) and dibenzo-18-crown-6 (II), shown below:

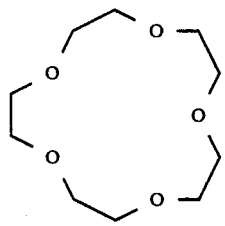

I

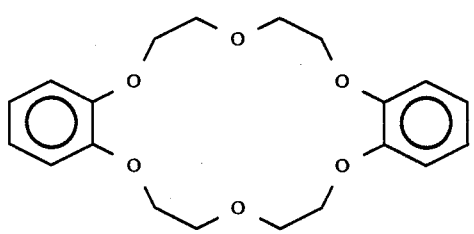

II

Also suitable for the detection of alkali and alkaline earth ions are cryptate-type ligands of the structure III

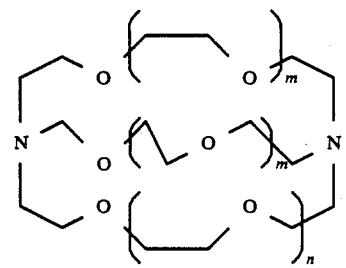

III where m and n are zero or integers from 1 to 5. See Lehn, 11 Acc. Chem. Res. 49 (1978).

Membrane ISEs for transition-metal ions such as $Fe^{+3}$ and $Ni^{+2}$ can be prepared in the manner set forth in Simone et al., 98 JACS 762 (1976) and Alcock et al., Dalton J.C.S. 394 (1978) from derivatives of thioethers such as 1,5,9,13-tetrathiacyclohexadecane (IV) and 1,5,9-trithiacyclododecane (V):

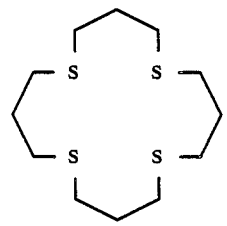 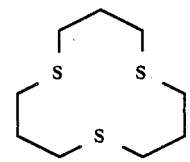

IV V

Also suitable for the detection of transition metal ions are derivatives of other macrocyclic ligands, such as 15,18-dithia-1,5,8,12-tetraaza-3,4,9,10,13,14,19,20-tetrabenzocycloeicosane-1,11-diene (VI):

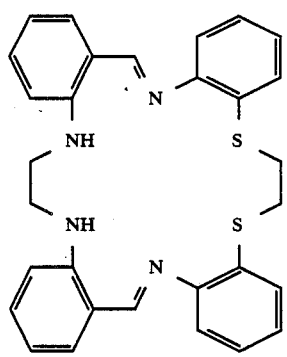

VI

For the preparation of ligands of the formula VI, see Taskar et al., 95 JACS 4163 (1973).

The amine and acid-chloride derivatives of the macrocyclic ligands that are used to prepare the interfacially-polymerized physicochemically functional membranes for ISEs may be easily synthesized by conventional techniques such as those set forth in Fieser et al., "Reagents for Organic Synthesis" (1967). For example, acid chloride groups may be added to saturated organic compounds by the chlorocarbonylation technique noted in Kharasch et al., 42 JACS 599 (1942), and they may be added to aromatic compounds by reaction with a diacid chloride under the Friedel-Crafts conditions reported in Sokol, 44 Org. Syn. 69 (1964).

Figure 2:
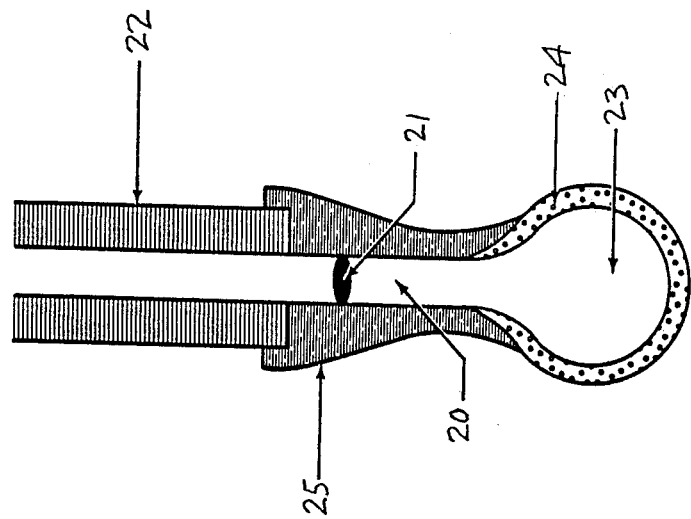
FIG. 2 is a schematic drawing of an ion-specific electrode of the present invention.

Physicochemically functional membrane ISEs may be prepared according to the present invention by a variation of the techniques developed for conventional (thick) polymeric membrane electrodes. See, for example, Cattrall et al., 43 *Anal. Chem.* 105 (1971). First, a piece of platinum wire (or other suitable conductive metal) 1 to 2 cm in length and about 0.05 cm in diameter is soldered to the end of shielded coaxial cable. A small metallic bead is formed at the tip of the platinum wire by gently melting it in a propane-oxygen flame. The platinum wire is then rinsed first in distilled water, then in acetone, and air dried. The metallic bead and about 0.5 cm of the platinum wire are then dipped in a 2 wt % aqueous solution of diethylenetriamine containing a small amount of surfactant to assure that the wire is wetted by the solution. Finally, the coated portion of the wire is dipped in a 2 wt % solution of the acid chloride derivative of complexing agent VI, for example, in hexane for 30 seconds, thereby forming a thin, metal-complexing polyamide film on the surface of the wire. After a final rinse and drying in air for 12 hours, the platinum wire is coated with a suitable insulator down to the tip of the coated bead, leaving the bead exposed. Such an exemplary fabrication is shown schematically in FIG. 2. The electrical potential of the wire, when dipped into a test solution containing a transition metal ion such as iron or nickel, will now be directly related to the metal ion concentration in solution. The sensor device, then, consists of the functional-membrane ISE and a separate reference electrode (not shown in FIG. 2) connected to conventional electronic equipment such as a voltmeter.

Oxidation/Reduction Potential Electrodes

Oxidation/reduction potential electrodes (ORPE) are also used in science and industry. These electrodes measure the relative oxidation/reduction potential of solutions and are useful in such applications as analytical chemistry, chemical process control, and waste treatment. An ORPE is simply an inert metallic electrode that serves to transfer electrons to and from a test solution. A simple platinum wire is frequently used as the electrode. However, as pointed out by Mann et al., in *Instrumental Analysis* (1974), the electrode surface can catalyze unwanted reactions and thus give an inaccurate response. Another problem with such electrodes is that they are very unstable and can drift 10 millivolts or more over a short time period due to changes in solution temperature, pH, or conductivity.

Inexpensive, stable, fast-responding, and very small ORPEs may be formed according to the present invention by coating a conducting wire with an interfacially-polymerized membrane containing suitable cryptate-type ligands with an entrapped metal ion. Examples of such ligands include those of structures VII and VIII, reported by Boston et al. in 95 *JACS* 4163 (1973) and by Larsen et al. in 11 *Inorg. Chem.* 2652 (1972),

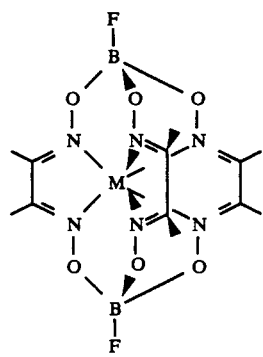

VII

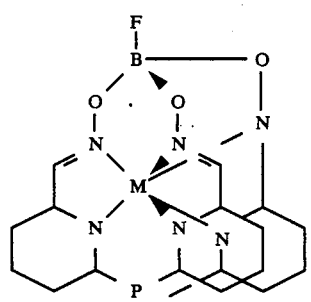

VIII where B is boron, F is fluoride, and M is a metal ion capable of forming a redox couple, such as $Ag(I)/Ag(II)$, $Co(II)/Co(III)$, $Cu(I)/Cu(II)$, $Ru(II)/Ru(III)$, $Ir(III)/Ir(IV)$, $Ni(II)/Ni(III)$, $Zn(I)/Zn(II)$, $V(II)/V(III)$, $Mn(IV)/Mn(VII)$, $Cr(III)/Cr(VI)$, and $Fe(II)/Fe(III)$. The best choice of redox couple to be used in an ORPE depends on the expected range of oxidation-reduction potentials to be encountered in use. For example, the $Zn(I)/Zn(II)$ couple has a standard reduction potential of approximately $-0.9$ V with respect to a standard Calomel electrode (SCE), and it would be useful to test solutions with low oxidation-reduction potential. Similarly, the standard reduction potential of the $Ag(I)/Ag(II)$ couple is approximately $+2.2$ V with respect to an SCE, and it would be useful to test solutions with high oxidation-reduction potentials. Even though the metal ion is entrapped in the ligand, it is physicochemically functional in that the ion can still be oxidized or reduced. Thus, the ratio of the concentration of metal ions in the two oxidation states in a membrane containing such metal-cryptate complexes will be a function of the oxidation/reduction potential of the test solution in which it is immersed. The ratio of concentrations determines the potential of the coated conducting wire, and hence provides the quantitative basis for determining the oxidation/reduction potential of the test solution.

A suitable method for preparing such solid state ORPEs is the same as that described for the preparation of ISEs, as is the method by which they may be incorporated into sensor devices.

Enzyme Electrodes

In some types of membrane electrodes, the initial reaction leads to the generation of a secondary product, which is then detected. An example is the enzymatic oxidation of glucose by glucose oxidase to produce carbon dioxide, which can then be detected by means of a $CO_2$-sensitive electrode. In such compound electrodes, the enzyme-bound membrane and the $CO_2$ sensor are intimately mounted within the same electrode housing.

Existing enzyme membrane electrodes do not have the enzyme moiety covalently bound to the membrane; in addition, the membrane components thereof are relatively thick. These characteristics result in enzyme electrodes that are unstable, have a short useful life, have slow response, and are relatively large.

An enzyme-based sensor may be fabricated according to the present invention in the following way. First, the sensing moiety, having physicochemical functionality which may be an enzyme such as glucose oxidase, may be covalently bonded to one of the reactants used to prepare interfacially polymerized polyamides, such as an amine. Other suitable enzymes include D-lactate dehydrogenase, alcohol dehydrogenase, glutamate dehydrogenase, L-alanine dehydrogenase, D-sorbitol dehydrogenase, glycerol dehydrogenase, carnitine dehydrogenase, xylose reductase, L-phenylalanine dehydrogenase, D-mannitol dehydrogenase, and alpha-amino acid transaminases such as glutamic-phenylpyruvic transaminase. A physicochemically functional interfacial polyamide membrane may then be formed by IP, by, for example, reaction of the physicochemically functional amine with, for example, a second reactant (such as a diacid chloride) that is reactive with the amine in a condensation reaction. A compound membrane electrode, of the type shown in FIG. 1, may then be fabricated from a conventional CO2 sensor and the enzyme-bound membrane. Specific examples of several alternative synthesis schemes for such an enzyme-bound membrane follow.

First, the enzyme may be separately reacted with an acid chloride and with an amine (for example, with two moles of acid chloride and with three moles of amine per mole of an enzyme E), and the two derivatized enzymes may be reacted interfacially to form a crosslinked enzyme membrane, as shown below:

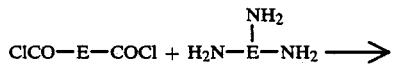

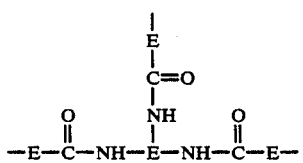

Alternatively, the enzyme may be separately reacted with an acid chloride and an amine, in the ratio of two moles of acid chloride to two moles of amine per mole of enzyme, the two derivatized enzymes being reacted by IP to produce a non-crosslinked membrane of the enzyme, as shown below

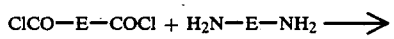

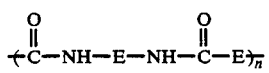

where n refers to the degree of polymerization

In a third method, the enzyme may be reacted with a diamine and the derivatized enzyme may be reacted interfacially with a diacid chloride (ClCO-R-COCl) to produce a thin, polymerized membrane of enzyme, as shown below:

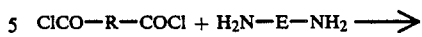

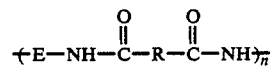

In each of these three reaction schemes, the enzyme E need not be a part of the polymer backbone. Instead, the interfacially polymerized membrane could be made with the enzyme pendant to the backbone, where it would be more effective in entering into its characteristic reactions due to the lack of steric hindrance:

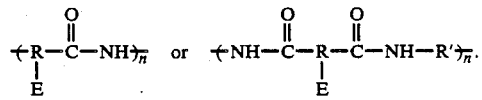

By carrying out any of the above three reactions on one surface of a CO2 electrode, the result would be a combination membrane/enzyme-based electrode capable of detecting the concentration of glucose in solution or in blood by catalyzing the oxidation of glucose to produce carbon dioxide gas, which gas would then permeate the thin enzyme membrane layer to be detected by the CO2 electrode.

Selective Membranes and Sorbents

The method of interfacial polymerization of physicochemically functional molecules can also be applied to the preparation of highly selective, high flux membranes and of sorbents for specific separations. To be commercially useful, membranes must combine high selectivity, i.e., they must transport one species to the exclusion of others, with high flux. Membranes made according to the present invention offer this combination. The same principles already described are used: (1) select a chemical moiety that is reversibly reactive with (e.g., by complexation) the desired chemical species; (2) derivatize that moiety into two complementary derivatives such that an IP reaction can be carried out between them; and (3) make an ultrathin membrane by IP on a suitable microporous substrate. The membrane will have the selectivity inherent in the original species-selective chemical moiety, and the membrane will exhibit very high flux because of its great thinness. If the membrane is made under conditions that lead to a crosslinked polymeric matrix, for example, by reacting a trifunctional-derivatized moiety with a complementary difunctional-derivatized moiety, the resulting membrane should also exhibit good stability.

In the event that it is desired to produce a selective sorbent composition, the IP reaction may be merely carried out at the interface of two immiscible solvents without a microporous support. Thus, in each instance below where there is described a chemical species-selective membrane comprising an interfacially polymerized physicochemically functional film and a microporous polymeric support, it is to be understood that the physicochemically functional film without a support may also be used as a species-selective sorbent. Such sorbent film may be used in a manner similar to the way in which ion-exchange resins are used, i.e., the film in granular form or on the surface of a support may be exposed to the fluid from which the desired species is to be removed.

Such physicochemically functional films comprise a thin polymeric network of reversibly reactive sites. The reversibly reactive sites can reversibly complex with a given species that is in turn transported through the film by a driving force such as a concentration gradient, a pH differential, or a pressure differential. The transported species may be neutral or ionic, gas or liquid, water-soluble or water-insoluble.

Broadly, such selective membranes are thin film composite membranes comprising a microporous support and the thin film interfacial polymerization reaction product of $M_FX_m$ and $NY_n$ wherein $M_F$ is a moiety having chemical species-specific reversibly-complexing complexing sites, N is a moiety not having any chemical species-specific complexing sites, X and Y are groups that are mutually reactive in a condensation reaction, and m and n are integers $\geq 2$. The X and Y groups that are mutually reactive in a condensation reaction are selected from any of the mutually reactive groups mentioned in "Background of the Invention" above, and are preferably selected from acid halides, amines, alcohols, aldehydes, thiols, isocyanates and sulfonyl halides.

Ion Transport and Sorption

An example of an interfacially polymerized physicochemically functional film of the present invention for the selective sorption or transport of zinc(II) ions is one containing zinc(II)-selective phosphate functional groups. An aqueous solution of the diamine organophosphate compound IX (where R is hydrogen or alkyl or aryl of 1 to 20 carbon atoms and R' is a covalent bond or alkylene of 1 to 10 carbon atoms) may be reacted under IP conditions with a polyfunctional acid halide such as terephthaloyl chloride (TPC) in an organic solvent, to form an ultrathin film of a phosphate-containing polyamide. When one of the R groups of compound IX is hydrogen, the other R group is alkyl, and R' is ethylene, compound IX is 2-ethyl(alkylphosphoryl)1,3-diaminopropane, and when reacted with TPC, the phosphate-containing polyamide X is formed.

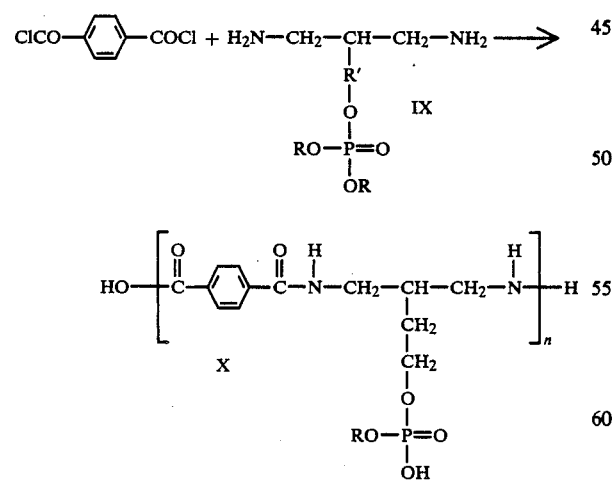

In this case, the organophosphate compound has incorporated into it diamine functionality, making it readily polymerizable with TPC. Alternatively, the organophosphate may be reacted with a trifunctional acid chloride such as trimesoyl chloride (TMC) to make a crosslinked polyamide structure. Organophosphates lacking amine functionality may be derivatized using standard techniques to render them reactive under IP reactions. In a different condensation reaction, the same phosphate-containing diaminopropane may be reacted in the same fashion with a polyfunctional isocyanate such as 1,4-diisocyanatobenzene or 1,3,5-triisocyanatobenzene, to form an ultrathin film. When the IP reaction is carried out with the diisocyanatobenzene, the phosphate-containing polyurea Xa is formed:

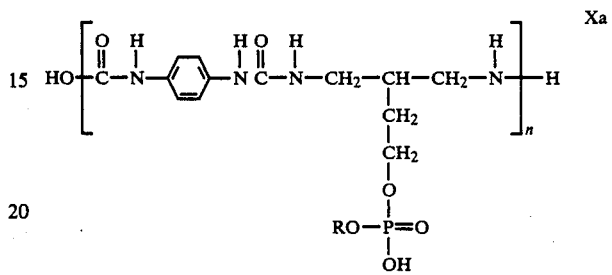

To make a useful membrane out of Compound X or Xa, the IP reactions may be carried out on one surface of a microporous support, as taught by Cadotte in U.S. Pat. No. 4,277,344. That is, the diamine organophosphate would first be dissolved in water, and the microporous support would then be contacted with a solution of the acid chloride in a water-immiscible solvent such as hexane, completing the preparation of the membrane.

Figure 3:
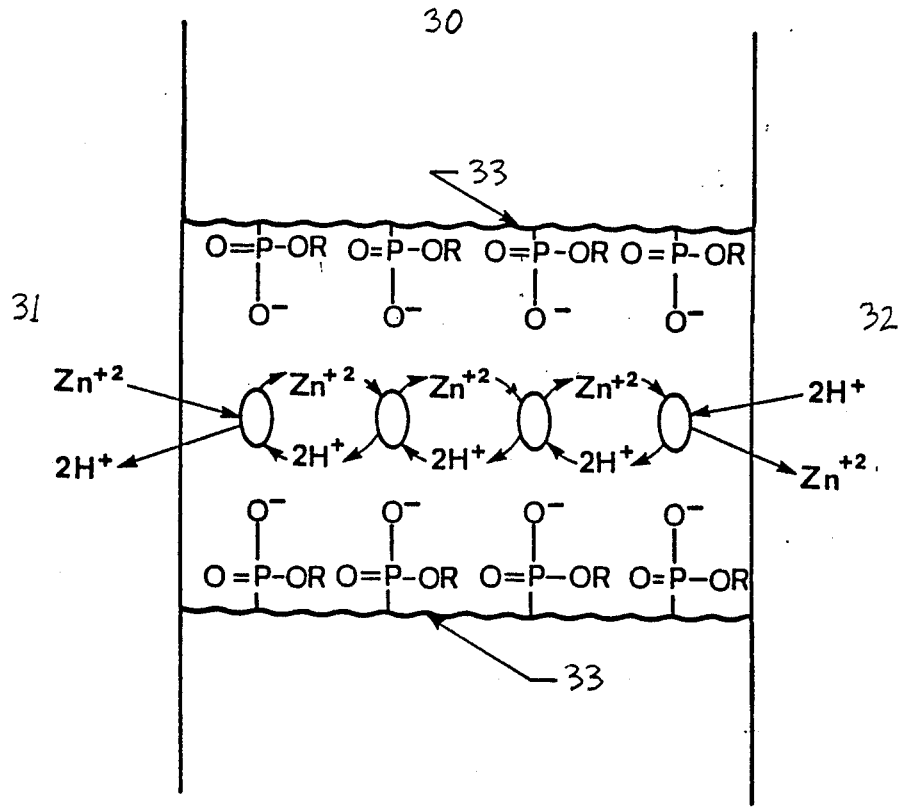
FIG. 3 is a schematic illustration of the operation of an exemplary application of selective membrane transport according to the present invention.

Such a physicochemically functional membrane could be used to separate $Zn^{++}$ ions from other ions and concentrate the $Zn^{++}$ ions at the same time, in a process called "coupled transport." See U.S. Pat. No. 4,437,994. The process is illustrated in FIG. 3. The membrane is interposed between a feed solution containing $Zn^{++}$ ions and other cations, such as $Fe^{++}$, from which it is to be separated. A pH gradient is imposed across the membrane such that the dilute feed solution is at a higher pH than the strip solution. At the higher pH, for example, pH $\geq 2$, $Zn^{++}$ ions are selectively extracted from the feed solution by the phosphate groups within the membrane. At the low pH on the opposite side of the membrane, i.e., pH $<1$, $Zn^{++}$ ions are released from the phosphate groups and enter the strip solution. Thus, there is a concentration gradient of $Zn^{++}$ ions within the membrane, causing transport of the ions from the feed solution to the strip solution. Because the flow of hydrogen ions through the membrane is coupled to the flow of $Zn^{++}$ ions in the opposite direction, the pH gradient can be used to "pump" $Zn^{++}$ ions "uphill," or against their concentration gradient in the two solutions, as is typical of coupled-transport membranes.

The same IP chemistry described above could be used to prepare a thin, selective sorbent for certain ions. For example, the organophosphate could be used to selectively remove $Zn^{++}$ or $Fe^{+++}$ ions from mixtures of ions, including $Ni^{++}$, $Cu^{++}$, $Na^+$, or $Ca^{++}$. The $Zn^{++}$ ion, for example, is sorbed by the organophosphate at pH $>2$, and it can be stripped off at pH $<1$. The advantages of the IP film over the organophosphate monomer, or some sorbent matrix impregnated with the organophosphate, are (1) the film contains a high concentration of the active agent, i.e., the organophosphate, (2) the film is stable and insoluble in solutions with which it would be brought into contact, and (3) the film would sorb and desorb the desired species quickly because of the rapid diffusion kinetics attendant with its thinness.

Another class of physicochemically functional membranes capable of selective sorption and selective transport of other metal ions that may be prepared according to the present invention are those containing crown ether metal-ion-complexing moieties. For example, a diamino crown ether compound such as di-(aminobenzo)18-crown-6 may be condensed with a polyfunctional acid halide such as TPC or a polyfunctional isocyanate compound under interfacial polymerization conditions to form an ultrathin polyamide film of the chemistry depicted by the reaction shown below, having metal-complexing sites available within the cavity of the 18-crown-6 moiety (XI):

functional membrane is capable of complexing metal salts by the general reaction

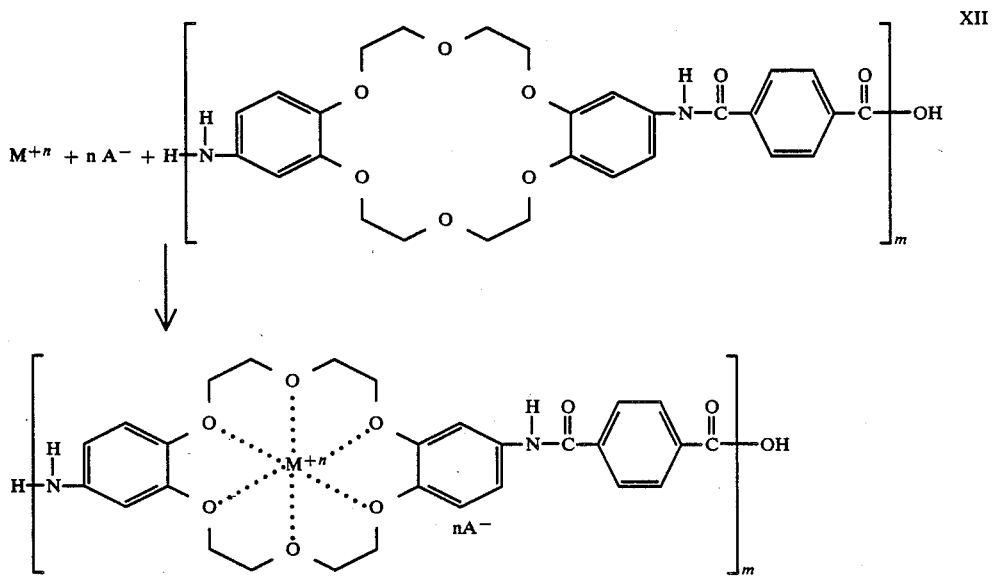

whereby the metal ion $M^{+n}$ is complexed within the cavity of the crown ether and the anion $A^-$ is loosely associated with the crown ether (XII), thus maintaining electrical charge balance. In membrane form, these polymerized crown ethers should exhibit good selectivity for certain ions over others, based on the binding ratios of the crown ether monomers. For example, the binding ratio of dibenzo-18-crown 6 for $K^+$ over $Na^+$ is 5.0, while that for $K^+$ over $Cs^+$ is 40. See Frensdorff, 93 *JACS* 600 (1971). When tested in the form of immobilized liquid membranes, the permeability ratio for $K^+$ over $Na^+$ for dibenzo-18-crown-6 is 16. See Tsukube, 23 *Tetrahedron Letters* 2109 (1982).

Another method of making such a physicochemically functional composite membrane is to condense the same

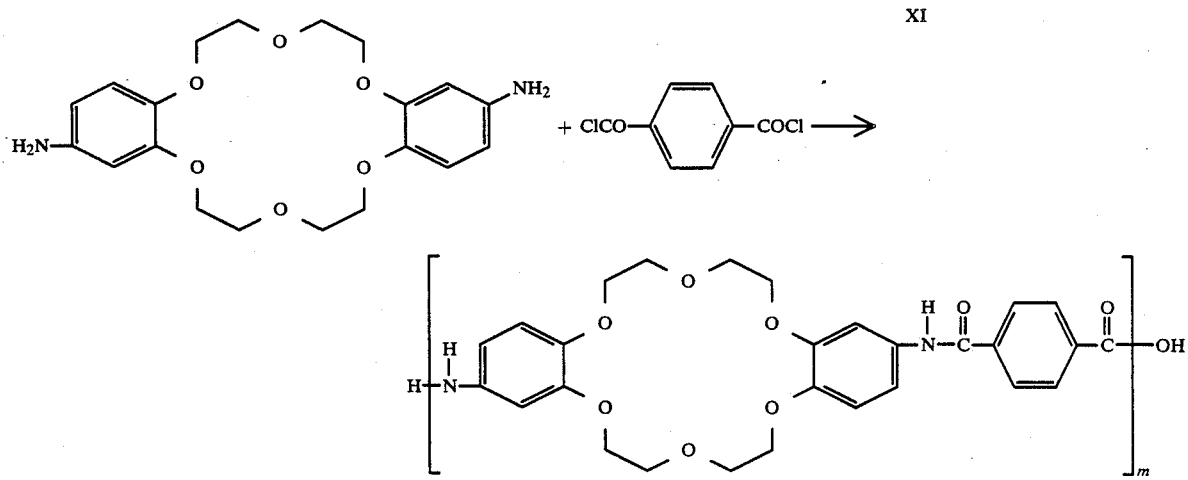

A composite selective transport membrane may be prepared by carrying out the IP reaction on one surface of a finely porous polymeric support, as described in U.S. Pat. No. 4,277,344. Such a physicochemically diaminobenzo crown compound with a polyfunctional isocyanate compound such as tolyldiisocyanate (TDI) under IP conditions to form, on a microporous support, an ultrathin polyurea membrane of the structure XIII depicted below, also having metal-complexing sites within the cavities of the 18-crown-6 moieties:

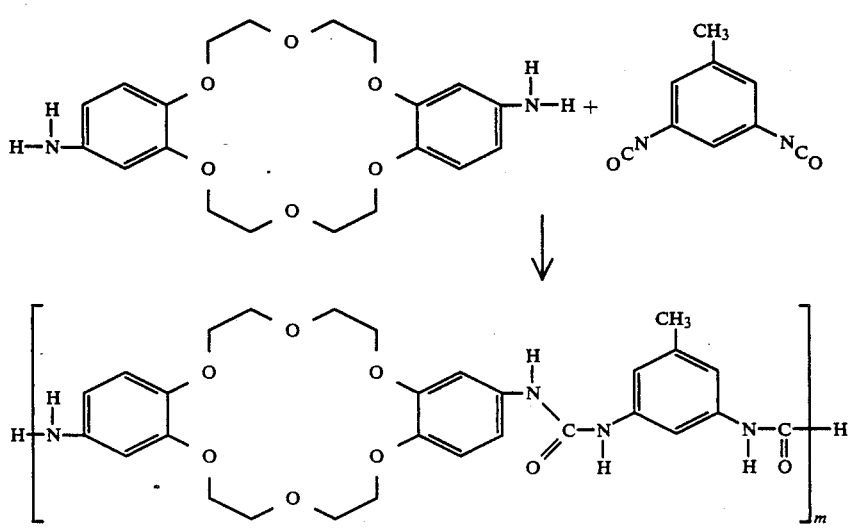

In use, the membrane would be placed in contact with a solution containing, for example, a mixture of $K^+$ and $Na^+$ ions, from which it is desired to separate the $K^+$ ions. On the opposite side of the membrane would be placed a solution of sulfuric or phosphoric acid. The $K^+$ ions would preferentially pass through the membrane and would be stripped from the membrane into the acid solution.

The same IP film could be used as a selective sorbent, using the same chemistry. That is, a crown ether in IP-film form could be used to strip $K^+$ ion from a solution of other cations. The $K^+$ could then be stripped from the sorbent film by contacting it with sulfuric or phosphoric acid.

Physicochemically functional composite membranes of the present invention may also be used for the selective sorption or transport of gases wherein one gas species is transported in preference to another intermixed with the first species, such as the transport of oxygen in preference to nitrogen in atmospheric air, as described below.

Oxygen and Carbon Monoxide

It is known that certain metalloporphyrins, certain metallo-Schiff base complexes, and certain metallophthalocyanines can selectively complex oxygen and that membranes containing these groups can selectively transport oxygen. See U.S. Pat. Nos. 4,451,270 and 4,542,010. In connection with the selective transport of oxygen over nitrogen see Hishide et al. in *Macromolecules*, Vol. 20, pp. 417–422 (1987), who describe such selective oxygen transport in a polymeric membrane containing Co(II) porphyrin groups. It is also known that certain metalloporphyrins such as cobalt(II) or iron(II) tetraphenyl porphyrin can selectively bind carbon monoxide. See Chang et al., 72 *Proc. Natl. Acad. Sci. USA*, 1166 (1975).

Such metallocomplexes may be incorporated into ultrathin films by the IP methods described herein. The metallo-Schiff bases are described in detail in commonly assigned U.S. Pat. Nos. 4,451,270 and 4,542,010, the descriptions of which are incorporated herein by reference, while the metalloporphyrins and metallophthalocyanines are described in detail in commonly assigned U.S. Pat. No. 4,784,736, the description of which is also incorporated herein by reference. The general structures of these metallocomplexes are shown below

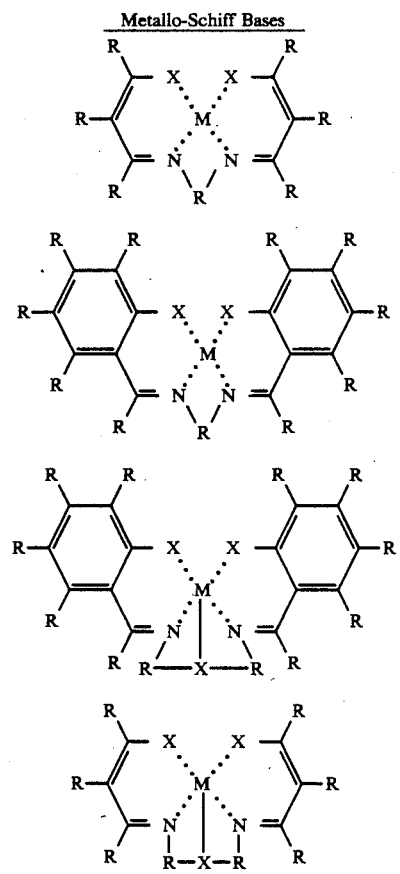

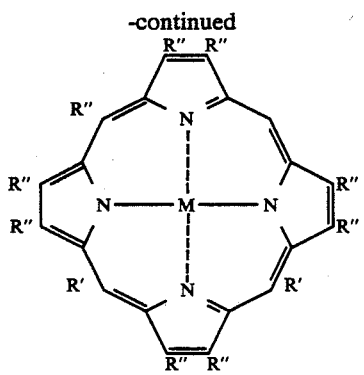

Metallophthalocyanines

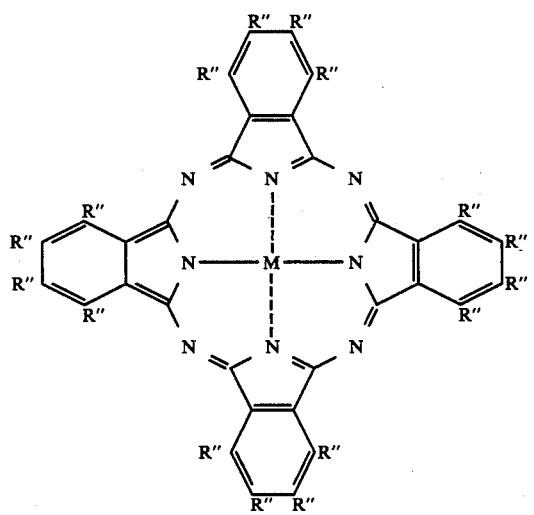

wherein M is a metal of +2 valence selected from cobalt, iron, copper, nickel, manganese, ruthenium and rhodium; X is

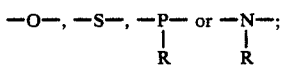

R is hydrogen, alkyl alkylene, aryl arylene, halogen, alkoxy or a nitrogen-containing moiety; R' is hydrogen, alkyl, aryl, pyridinyl, R", alkyl-R", or aryl-R"; R" is hydrogen, Hal, $NH_2$, $CH_2NH_2$, SH, OH, COHal, COOH, NCO, or $SO_2Hal$; and Hal is a halide.

An exemplary method of preparing a metalloporphyrin and incorporating its oxygen- or carbon monoxide-complexing physicochemical functionality into an interfacially polymerized membrane follows. The tetracarboxylic acid derivative of tetraphenylporphyrin, 5,10,15,20-tetra(P-carboxyphenyl) porphyrin was converted to its acid chloride derivative by refluxing 1 gram of the porphyrin in 50 ml of thionyl chloride for 16 hours. Excess thionyl chloride was removed by vacuum distillation until the solid residue appeared to be dry. A vacuum of 1 torr was applied at 50° C. for 20 minutes to remove the last traces of thionyl chloride and HCl produced by the reaction. The conversion of carboxylic acid groups to acid chloride groups was inferred from the subsequent characteristic reactivity of the product with amines to form a polymer. This acid chloride derivative of the tetraphenylporphyrin was interfacially polymerized with diethylenetriamine (DET) on a microporous support by a three-step process.

First, a microporous polypropylene support comprising a film about 25 microns thick was clamped between two 2.5-inch-ID polypropylene annular rings. This assembly was then placed in a petri dish that contained a $10^{-3}M$ solution of the acid chloridederivatized tetraphenyl porphyrin monomer in chloroform. The level of the porphyrin solution was adjusted so that it coincided with the upper surface of the microporous support. Second, the reservoir formed by the upper ring was filled with a $10^{-3}M$ aqueous solution of DET. The interfacial polymerization reaction then proceeded at the chloroform-water interface. Finally, the reaction was stopped after 30 minutes by removing the upper aqueous layer, leaving the polyporphyrin film on top of the microporous support. Prior to characterizing the film, the upper and lower surfaces of the microporous support were washed alternately with chloroform and water to remove any of the unreacted monomers.

The resulting polyporphyrin film was converted to the cobalt(II) porphyrin form by placing the film in a solution of 0.1 g cobalt(II) chloride in 100 ml dimethylsulfoxide at 80° C. for 16 hours. Conversion of the free base porphyrin polymer to the cobalt(II) porphyrin polymer was evidenced by the disappearance of the four Q bands characteristic of the metal-free porphyrin, and by the appearance of the alpha and beta bands characteristic of the metal-containing porphyrin, in the region of the UV/visible spectrum between 400 and 700 nm.

The reversible oxygen-sorbing property of the cobalt(II) porphyrin polymer was demonstrated by the following experiment. The cobalt/porphyrin polymer film was placed in a DMSO solution containing a large excess of the axial base dimethylaminopyridine (DMAP) (the molar ratio of DMAP to porphyrin was about 2000). An "axial base" donates electrons to the coordinated metal, thereby improving the reversible oxygen-binding capacity of the metallo-porphyrin. After two hours, the cobalt/porphyrin polymer film was removed from the DMSO solution, rinsed in chloroform, and then air dried. The cobalt/porphyrin polymer film was then placed in a gastight cell equipped with an inlet and outlet port so that the cell could be purged and pressurized with a gas. The polymer film was then exposed to 75 psia of oxygen at room temperature. The Soret band, originally at 418 nm, shifted to 444 nm. This peak shift, characteristic of the formation of an oxygen complex (see Bengelsdijk et al., 97 JACS 22 (1975) and Nishide et al., 19 Polm. J. 7 (1987)), occurred within seconds after exposure to the oxygen. After three minutes the oxygen was flushed from the cell with nitrogen. The spectrum reverted to its original pattern within one minute. The film was cycled between oxygen-loaded and oxygen-unloaded states several times. The oxygen-loaded polymer film always exhibited the Soret band at 444 nm while the oxygen-unloaded polymer film always showed the Soret band at 418 nm, indicating the film reversibly sorbed and desorbed oxygen.

As another example of how to incorporate the selective oxygen-complexing physicochemical functionality of a metallo-porphyrin such as iron(II) porphyrin into a membrane, a solution of a metallo-porphyrin such as tetra(aminophenyl)-porphyrin iron(II) in water or dimethylsulfoxide (DMSO) or other suitable solvent may be held within the pores of a microporous polymeric support membrane and then exposed to a solution of an acid halide such as fumaryl chloride in a hydrocarbon solvent such as hexane to form an ultrathin polymeric membrane on the surface of the support containing recurring units of structure XIV

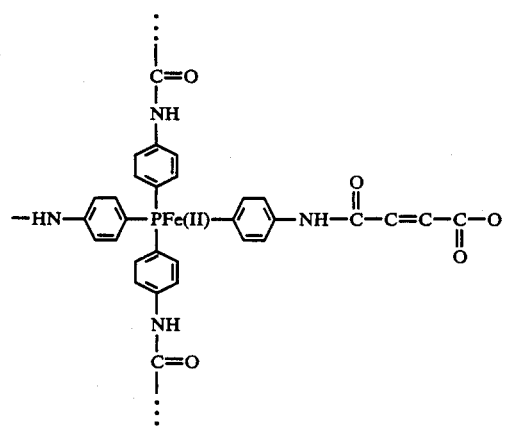

where PFe(II) is iron (II) porphyrin. Similarly, an aqueous solution of tetra-(aminophenyl)-porphyrin iron(II) may be reacted with a solution of an iron(II) porphyrin acid halide such as tetra(carboxyphenyl acid chloride)-porphyrin iron(II) in methylene chloride, to yield a supported ultrathin polymeric membrane containing slightly more (i.e., 10 to 20%) porphyrin groups per unit weight than structure XIV in recurring units of the structure XV.

complementary derivatives of the metallo-Schiff base moiety are prepared, which are then reacted by IP.

For example, the first derivative may have the general structure XVI

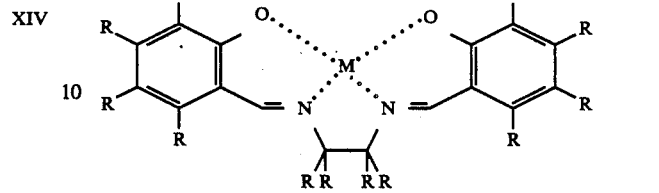

where at least two of the R groups are condensation-polymerizable functional groups (i.e., $NH_2$, NHR, OH, NCO or COX where X is halide) or alkyl or aryl groups substituted with condensation-polymerizable functional groups, and the remaining R groups are selected from alkyl, aryl, alkoxy, aryloxy, nitro, halide, ketoxy, and amino. The second derivative may be essentially any compound that has two or more condensation-polymerizable functional groups that have complementary reactivity with the functional groups of the first derivative. Alternatively, one of the two reactants in the condensation reaction need not be a metallo-Schiff base. The polymer is formed as the polycondensation reaction product of the two reactants, the reaction taking place at the interface between two immiscible solvents, one containing the first reactant and the other containing the second reactant, on one surface of a microporous support. The poly-Schiff base can subsequently be converted to a polymetallo-Schiff base by contacting the

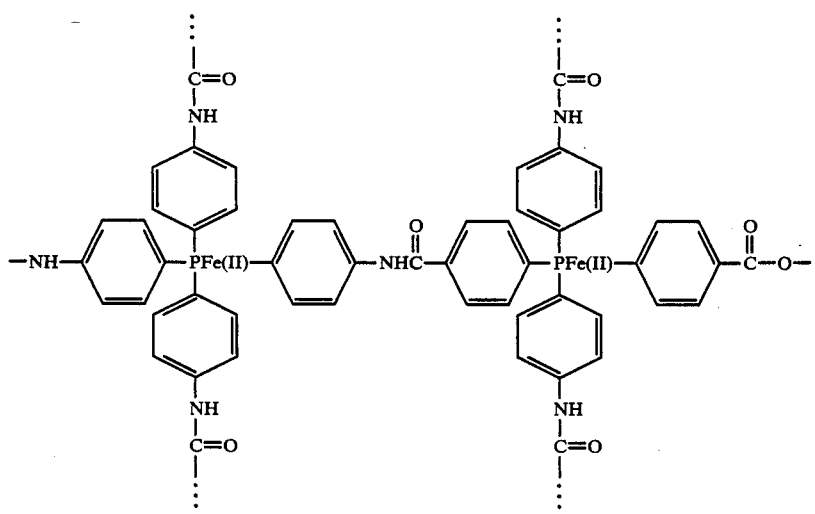

Oxygen-transporting membranes can also be made from metallo-Schiff base compounds by the IP process. The incorporation of metallo-Schiff base complexes into an ultrathin membrane may be accomplished by the same general method described earlier. That is, two polymer with a metal salt in the presence of a base.

An example of the formation of a polymetallo-Schiff base is the IP reaction, on the surface of a microporous support, of the diamine-functionalized cobalt-Schiff base XVII with a diacid chloride to form the polymeric Schiff base XVIII, as shown below:

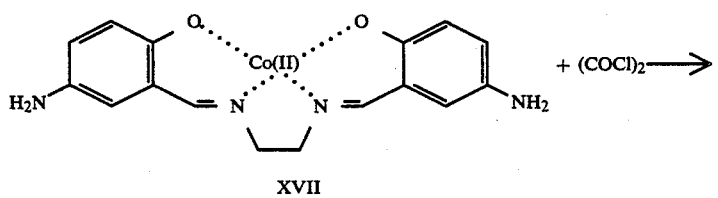

XVII

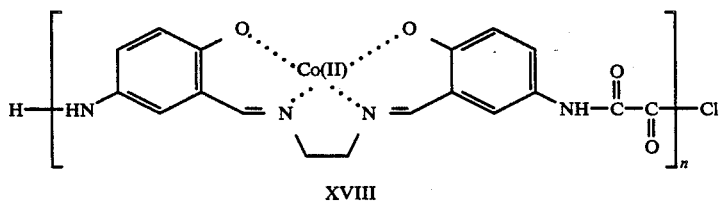

XVIII

Oxygen is reversibly bound by the polymeric Shiff base in the presence of an axial base, B, to form the adducts XIX and XIXa, according to the invention:

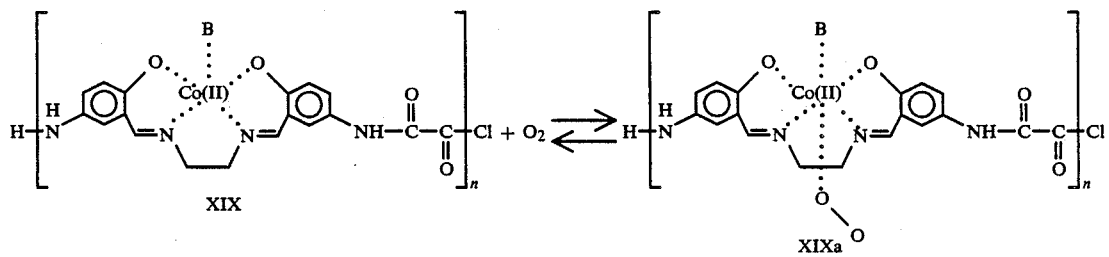

where B is an axial base selected from imidazoles, ketones, amides, amines, sulfoxides, pyridines and Lewis bases containing secondary or tertiary nitrogens. Preferred examples of axial bases include 1-methylimidazole, 2-methylimidazole, 1,2-dimethylimidazole, dimethylsulfoxide, N,N'diethylenediamine, 4-dimethylaminopyridine, 4-aminopyridine, pyridine, 4-methylpyridine, 4-methylaminopyridine, 3,4-lutidine, 3,5-lutidine, 4-cyanopyridine, 4-methoxypyridine, 4,4-bipyridine, pyrazine, 4-pyrrolidinopyridine and N-methylpyrazinium halides.

Other moieties that can reversibly bind oxygen and can be incorporated into polymeric thin films according to the present invention include metallophthalocyanines and other transition metal complexes with four electron-donor atoms.

The oxygen-sorbing membranes described above may be used to extract oxygen from air as follows. One side of the membrane, the feed stream, side is placed in contact with air at atmospheric pressure. The other side of the membrane, the product stream, side is evacuated by means of a vacuum pump. The pressure differential this produces provides a driving force for gas permeation across the membrane. Because the membrane is much more permeable to oxygen than to nitrogen, the gas permeating the membrane will be enriched in oxygen. The process may also be carried out by pressurizing the feed stream and removing the oxygen-enriched air in the product stream at some lower pressure.

All of the oxygen selective materials described above could also be used as selective sorbents. In use, the IP films would be exposed to a mixture of oxygen and other gases, such as air, at a pressure greater than atmospheric pressure. The oxygen would be selectively sorbed by the thin film. The pressure would then be reduced to atmospheric or less than atmospheric and the oxygen would be stripped off of the sorbent film.

It is also known that metalloporphyrins such as cobalt (II) and iron (II) tetraphenyl porphyrin can selectively bind carbon monoxide. See Chang et al., 72 Proc. National. Acad. Sci. USA, 1116 (1975). Thus, the Co(II) or Fe(II) tetraphenyl porphyrin membranes described above could be used to transport carbon monoxide gas, and effect a separation between CO and $H_2$, for example. Mixtures of CO and $H_2$ are produced in the "shift reaction" wherein methane is reacted with water vapor to produce a CO-$H_2$ mixture, from which $H_2$ can be beneficially extracted. That separation is now done by adsorbing the CO, but it could also be carried out with the CO-selective membrane described herein. The CO-transporting membrane would be used in the same way, i.e., by establishing a gradient in the partial pressure of CO across the membrane, CO selectively permeating the membrane.

The same CO-selective IP film could be used as a selective sorbent. In use, the Co(II) or Fe(II) tetraphenylporphyrin film would be exposed to a CO-containing gas stream at pressure. The CO would be selectively sorbed. It would then be stripped off by reducing the pressure.

Carbon Dioxide and Hydrogen Sulfide

Two other gases of major industrial importance that can be recovered by the present invention from mixtures in which they are commonly found are carbon dioxide and hydrogen sulfide. Both gases are frequently present in sources of natural gas, and they must be separated from the methane of natural gas before the gas can be transported by pipeline. The separation is now carried out with amine scrubbers or, in some modern plants, with selective polymeric membranes made of cellulose acetate or polysulfone. Those two "sour gas"

components can also be removed from natural gas by means of membranes made from certain complexing agents by the IP process of the present invention.

Selective binding of the acid gases carbon dioxide and hydrogen sulfide is particularly efficient with pyrrolidone-type complexing agents of the general formula XX

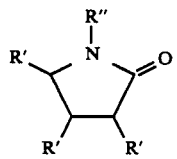

XX wherein R' is hydrogen or R"; and R" is alkyl, aryl, cycloalkyl, substituted alkyl, substituted cycloalkyl, or substituted aryl, of 1 to 20 carbon atoms. Substituents on the alkyl chains, the cycloalkyl rings and the aryl groups in the pyrrolidone formulas can include nonreactive groups such as hydroxy, amino, halide, and ether groups. Specific examples of preferred pyrrolidone complexing agents include N-methy-2-pyrrolidone, N-cyclohexyl-2-pyrrolidone, 5-methyl-N- cyclohexyl-2-pyrrolidone, and N-alkyl pyrrolidones where the N-alkyl group is added to the pyrrolidone by condensation of an alcohol obtained by hydrolysis of tallow or coconut oil fatty acids, commonly known as N-tallowalkyl-2-pyrrolidone and N-cocoalkyl-2-pyrrolidone, respectively.

An example of how a polypyrrolidone membrane can be fabricated is the reaction at a liquid-liquid interface between immiscible solutions of the reactants, of the amine-functionalized pyrrolidone XXI with a diacid chloride to form the polycondensation product XXII, shown below

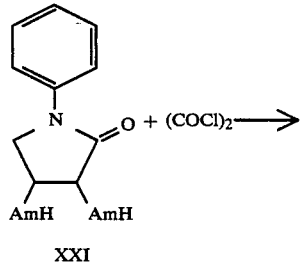

XXI

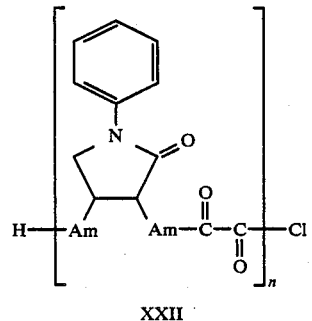

XXII where Am is —CH$_2$—NH—.

A membrane consisting of the polymerized pyrrolidone moiety shown above may be used to extract CO$_2$ or H$_2$S from natural gas by exposing one side of the membrane to the natural gas at pressure while the other side is exposed to the atmosphere. The membrane will allow CO$_2$ and H$_2$S to pass through, while retaining the CH$_4$, thus effecting a clean separation.

The same IP pyrrolidone film could be used as a selective sorbent for CO$_2$ or H$_2$S. In use, the film would be exposed to a high pressure of natural gas, containing CO$_2$ and H$_2$S, for example. The two acid gases, CO$_2$ and H$_2$S, would be sorbed by the selective sorbent, and they could then be removed by lowering the pressure. This process is akin to the well-known pressure-swing adsorption process for gas separations.

Ammonia

Another important gas separation to which the present invention can be applied is the separation of ammonia from other gases, and especially the separation of ammonia from nitrogen and hydrogen in ammonia synthesis. Ammonia is selectively and reversibly bound by a wide variety of cyclic copper complexes including, for example, macrocyclic beta-diketone ligands of the type disclosed by Alberts et al. in 101 JACS 3545 (1979) and exemplified by 3,5,15,17-tetraoxo-1,7,10,13,19,22hexaoxacyclotetracosane (structure XXIII);

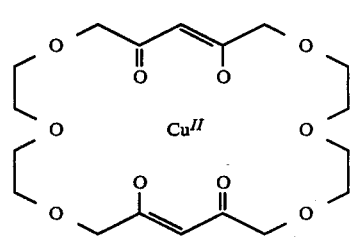

XXIII and by tetraazamacrocyclic compounds of the type disclosed by Muller et al. in 23 Tetrahedron Letters 2769 (1982) and exemplified by complexes of the structure XXIV, XXV, and XXVI

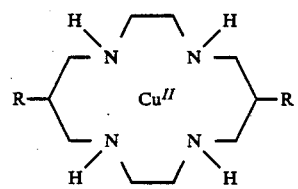

XXIV

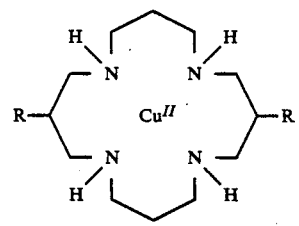

XXV complexing functionality, the chemical structure being as shown in structure XXIX.

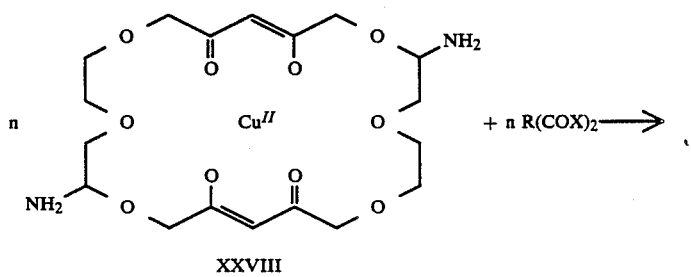

XXVIII

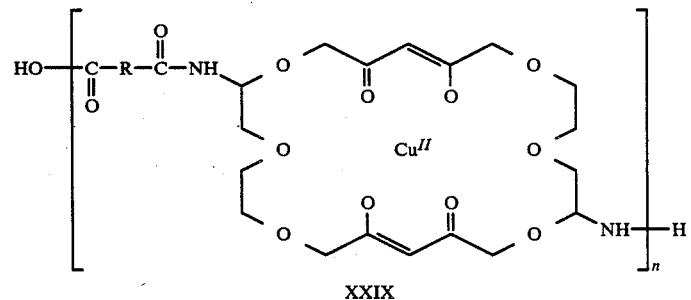

XXIX

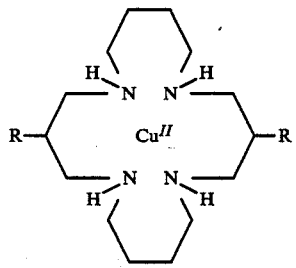

wherein R is selected from hydrogen, alkyl of 1 to 20 carbon atoms, or aryl; and by thioimino cryptands of structure XXVII.

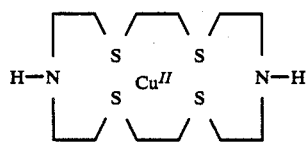

XXVII

While selective transport of ammonia through membranes has not been demonstrated for each of the above-mentioned cases of selective binding, there is sufficient evidence to conclude that membranes that selectively and reversibly bind one species in a gas mixture will also selectively sorb or transport that species, and thus effect a separation of the gaseous species.

Composite membranes having reversible ammonia-binding capacity may be prepared by interfacially polymerizing on a microporous polymeric support the diamine derivative of any of structures XXIII through XXVII with a diacid halide to form a composite membrane having an ultrathin layer containing repeat units of the ammonia-complexing functionality. For example, the diamino copper cryptate 8,20-diamino-3,5,15,17-tetraoxo1,7,10,13,19,22-hexaoxacyclotetracosane (structure XXVIII) may be interfacially polymerized with a diacid halide to form an ultrathin polymer layer containing repeat units of the copper cryptate-ammonia- In the above reaction scheme, R can be a covalent bond, alkylenyl of 1 to 20 carbon atoms, or arylenyl; X is a halide group; and n is an integer representing the degree of polymerization. It should be understood that the amine-acid halide condensation reaction is chosen for purposes of illustration only, and that any of the other known types of reactive moieties used in condensation reactions noted above under the heading "Background of the Invention" may also be used.

Other examples of the preparation of functional membranes made by IP that are capable of physicochemically selectively transporting ammonia are the reaction of any of the complexes XXIV-XXVI above with a diacid halide of the formula $R(COX)_2$ where R and X are as defined above. Since such complexes already contain secondary amino groups, no intermediate reaction to add amino groups is necessary, and so they may be reacted directly with an acid halide under interfacial polymerization conditions to form the polymeric film containing the corresponding functional groups shown in structures XXIV-XXVI. For example, reaction of a diacid halide with structure XXIV will yield an ultrathin film of the structure XXX.

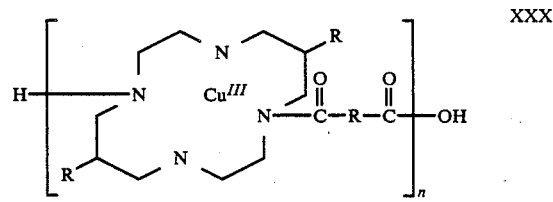

XXX

In use, the ammonia-selective membrane would be placed in contact with an ammonia-containing gas stream, such as the off-gas from an ammonia-synthesis stream. ammonia would preferentially permeate from the high-pressure side to the low-pressure side of the membrane.

The same IP ammonia-complexing agents can be used as selective sorbents in film form. The film would be exposed to an ammonia-containing gas stream at pressure, allowing ammonia to be sorbed. Ammonia would be stripped off at a lower pressure. If the ammonia were dissolved in an aqueous solution, it would be loaded into the selective sorbent at a pH where it exists in neutral form, i.e., at pH >10, and it would be stripped off at pH <9.

Olefins

Another industrially important separation to which the present invention may be applied is the separation of olefinic hydrocarbons from paraffinic hydrocarbons. Olefins have a number of uses, including as monomers used in the synthesis of polymers, such as polyethylene. They are separated from hydrocarbon mixtures by distillation; however, polymeric membranes made according to the present invention could also be used. Certain silver or copper complexes are known to bind olefins. See Matson et al., 38 *Chem. Eng. Sci.* 503 (1983); Kimura et al., "Recent Developments in Separation Science," Vol. 5, page 11 (1979); LeBlanc et al., 6 *J. Memb. Sci.* 339 (1980); Hughes, et al., "Olefin Separation by Facilitated Transport Membranes," presented at the *Spring National AIChE Meeting,* Houston (1981); and U.S. Pat. No. 4,318,714. Silver and copper sulfonate complexes, for example, are known to selectively and reversibly bind olefins. A membrane possessing such a functionality may be prepared by reacting tolyl diisocyanate sulfonate with, for example, a diol such as diethylene glycol under IP conditions on a microporous polymeric support to yield a composite membrane comprising the support with an ultrathin layer of a polymer composition having repeat units of structure XXXI.

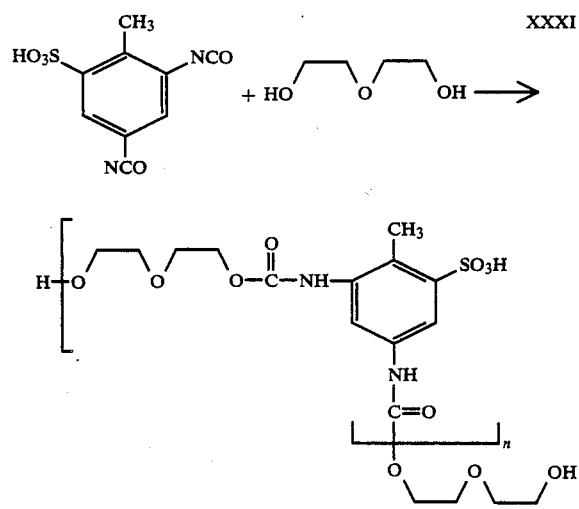

This reaction is then followed by exposing the membrane to silver(I) or copper(I) ions to obtain the silver or copper sulfonate complex at each sulfonate site in the ultrathin film (XXXIII) as shown below $nM^+$ +

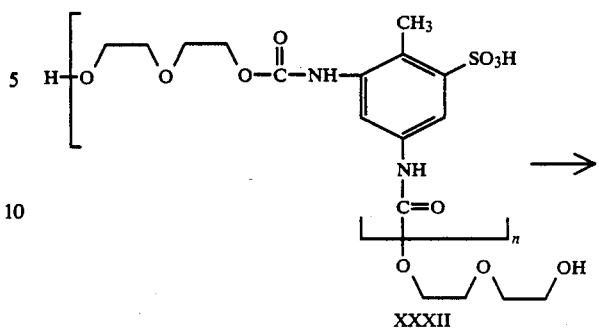

where M is selected from silver and copper.

Any hydrocarbon containing at least one carbon-carbon double bond, commonly referred to as an olefin, will then complex at the silver- or copper-complexed sites. Again, of course, it should be understood that any combination of mutually reactive moieties in a condensation reaction of the types discussed above may be used to achieve the same result. The central point is that an ultrathin, physicochemically functional, polymeric membrane can be formed that contains $Ag^+$ (or $Cu^+$) complexing sites that will reversibly and selectively bind olefins, thereby selectively sorbing/transporting olefins.

In practice, these membranes may be used by exposing one side of the membrane to a gaseous or liquid mixture of olefins and paraffins. A pressure differential may be established by evacuating the downstream side of the membrane, allowing the olefins to pass through while retaining the paraffins.

The same IP olefin-selective film could be used as a selective sorbent. In use, the film would be exposed to an olefin-containing gas stream at pressure. The olefin would be stripped off by reducing the pressure.

Biocompatible Materials

Current artificial organs, drug implants, and other materials that contact blood must be made of extremely inert polymers or other inert materials to avoid blood coagulation or thrombogenicity. In many cases, foreign-body rejection, encapsulation, or abscess formation occurs in spite of the best precautions. In attempts to achieve biocompatibility of implants, researchers have investigated attaching heparin or other anticoagulants to the surface of artificial organs or other polymeric implants. Heparin is known to be an effective anticoagulant, but adding heparin directly to blood leaves the patient susceptible to severe bleeding. Thus, it is desirable to immobilize the heparin while retaining its efficacy. See Falb, "Surface-Bonded Heparin," in *Polymers in Medicine and Surgery*, page 77 (1975).

Two primary methods have been used to attach heparin to surfaces: (1) ionically bonding heparin to quaternary ammonium salts attached to the polymeric surfaces; or (2) covalently bonding heparin derivatives directly to the polymeric surfaces. See, for example, Ebert et al., "The Anticoagulant Activity of Derivatized and Immobilized Heparin," in *Biomaterials: Interfacial Phenomena and Applications*, page 161 (1982). In the first case, heparin gradually dissociates from the quaternary ammonium salts (in a typical example 75% of the heparin is lost after one week's contact with blood), and so the heparinized surface has a lifetime that is too short for many applications. In the second case, the heparin remains on the surface, but typically suffers from a reduced efficacy due to steric or chemical interference with heparin's role in binding thrombin to inhibit coagulation, the interference being caused by the heparin derivative or the polymeric surface to which it is bound. In addition, a different heparin derivative must be used for each type of polymer surface to achieve satisfactory bonding.

If a poly-heparin coating could be applied to such surfaces, the heparin would remain on the surface, thus avoiding the disadvantage of the ionically-bound heparin; the heparin activity would be maintained because the heparin coating would cover the entire surface rather than discrete bonding sites; and the coating could be applied to virtually any relatively uniform surface, including non-polymeric surfaces, so that a single type of coating could be easily used for a number of different types of devices. Furthermore, if the coating is applied sufficiently thinly it would minimize any interference with the desired transport to or from the surface of, for example, drug-releasing implants or implanted sensors. Each of these advantages may be realized by the present invention.

Heparin is a polysaccharide consisting of alternating glucosamine (G) and glucuronic acid (GA) residues. The glucosamine moiety itself possesses amine functionality, which can be utilized in an IP reaction with a diacid halide, diisocyanate, or dialdehyde to form a crosslinked poly-heparin membrane. For example, according to the present invention heparin may be dissolved in an aqueous solution, adipoyl chloride may be dissolved in an organic solution such as benzene, and a poly-heparin membrane would form at the interface between the two solutions. The reaction is illustrated below:

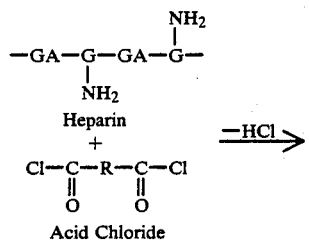

-continued

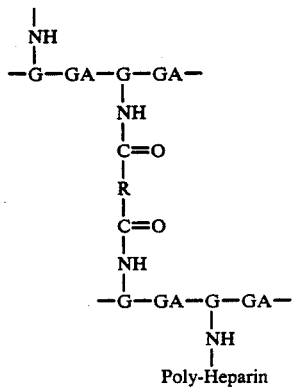

To place this coating on an indwelling catheter that must remain in the body for several weeks, for example, the catheter may be dipped sequentially in an aqueous solution containing 0.1 to 5.0 wt% of the sodium salt of heparin followed by an organic solution containing 0.1 to 5.0 wt% adipoyl chloride, whereupon a poly-heparin membrane would form on the surface of the catheter. If the catheter is hydrophobic, a better coating would be obtained by dipping in the organic solution first, followed by the aqueous solution.

It has been postulated that the higher-molecular-weight fractions of heparin possess more activity than the lower-molecular-weight fractions. A poly-heparin membrane might be expected, therefore, to exhibit a greater degree of activity, due to its higher molecular weight and the relative absence of low- molecular-weight fractions. In addition, the loss of heparin activity in vivo has been associated with the presence of free amino groups. See, for example, Ehrlich et al., 62 *J. Pharm. Sci.* 517 (1973). Formation of poly-heparin through a condensation reaction of the free amino groups with an acid halide, for example, would thus retard or prevent loss of activity. Finally, heparin activity has been correlated with the number of its free carboxyl groups. See Ebert et al., Ibid. A polyheparin membrane prepared as above retains all of its carboxyl groups, in contrast to the method of covalent bonding of heparin to polymeric surfaces through the carboxyl groups.

Targeted Drug Delivery

The present invention also has utility in the field of targeted drug delivery by parenteral, oral, subcutaneous, or intramuscular administration. Antibodies bound to the surface of microparticles can cause those microparticles to interact with specific tissues, thus delivering the therapeutic contents of the microparticles to those tissues.

Recent research has been aimed at bonding antibodies or other cell- or tissue-specific agents such as immunoglobulins to the surface of drug-containing microparticles to achieve targeting of the microparticles. See Illum et al., "Attachment of Monoclonal Antibodies to Microspheres," in Volume 112 of *Methods in Enzymology: Drug and Enzyme Targeting*, page 67 (1985). One of the problems of such a process is that a different bonding mechanism must be used in each case, depending on the chemical structure of the microparticle polymer. Several techniques have been developed for different chemistries, with varying degrees of effectiveness.

None is suitable as a general method of permanently adhering antibodies to a wide variety of microparticles. Since it is important in many cases to select the polymer for the microparticles based on its permeability or other functional considerations, a general method of adhering antibodies to microparticles would be useful. The present invention provides such a general method, since a functional poly-antibody coating can be applied directly to the microparticle surface; the method is not dependent on the nature of the microparticle polymer.

A poly-antibody coating may be made by contacting an aqueous solution containing the antibody with an organic solution containing, for example, a dialdehyde, a diacid halide, or a diisocyanate. A product useful for targeted drug delivery may be made in this manner by dissolving an organic-solvent-soluble dialdehyde such as 4,4'-(hexamethylenedioxy)dibenzaldehyde, together with a polymer such as cellulose acetate, and a drug such as an antineoplastic agent, in an organic solvent such as acetone. This solution is then emulsified in an aqueous phase containing an antibody such as anti-osteogenic sarcoma monoclonal antibody. The dialdehyde reacts with the amino groups of the antibody at the surface of each microdroplet in the emulsion, thereby linking the antibodies together in a coating around the microdroplet. The organic solvent is then evaporated from the microdroplets, precipitating polymer-drug microparticles with an aldehyde-linked-antibody coating. The coating is thus a "polyantibody." Such coated microparticles may be suspended in normal saline and injected intravenously into the patient to be treated. Microparticles' injected in this manner would reach the target tissue (sarcoma cells, for example) and have the opportunity to bind to that tissue before reaching the reticuloendothelial system, which traps all circulating particles. The drug would then be released in proximity to the target tissue, increasing efficacy and decreasing the toxic side effects caused by nonspecific systemic administration.

Narrow Band Optical Absorber

Another application of the present invention lies in the fabrication of a narrow band optical absorber. Such an absorber could be used in a receiver of signals transmitted at optical frequencies or as an optical filter to block out unwanted optical frequencies from a transmitted beam of light. For example, in communications with amplitude-modulated laser light, the signal is essentially monochromatic. Receivers are needed that are tuned only to the laser light wavelength, and which are insensitive to background sunlight or man-made polychromatic light. Currently, most receivers employ a grating or prism monochromator to filter out unwanted optical wave-lengths. These are complicated devices, whereas a thin film receiver according to the present invention is compact and simple.

It is known that coatings of strongly absorbing dyes on the base of a prism exhibit intense absorption over an exceedingly narrow band. See Babcock et al., 62 *J. Chem. Phys.* 700 (1985). The wavelength of absorption depends upon the thickness of the film and the angle of incident light. The IP technique set forth above may be used to coat one side of a prism with a strongly absorbing dye such as a polyporphyrin. The ultrathin polyporphyrin film could be applied by, for example, dipping the base of the prism through the interface of the two immiscible liquids containing the reactive porphyrin moieties, akin to the method used to pick up Langmuir-Blodgett films onto glass slides. The resulting film could act as a generator of current modulated by the intensity of the incoming light, because the incoming light would photoionize the polyporphyrin, causing a transmembrane potential to develop, thus producing a small electrical signal. The signal could be picked up by means of conducting wires on opposite sides of the film, then amplified by conventional techniques and then transduced to yield a readable sound or optical signal, i.e., the assemblage could be used as a communication tool.

The method of the present invention is particularly well-suited to this application since, in order to be useful in such a device, the dye film must be of a thickness comparable to the wavelength of light in the material, i.e., on the order of a few hundred to a few thousand Angstrom units thick, and it must be of a uniform thickness. Using the IP method with reactive light-absorbing dye moieties, a thin light-absorbing dye layer may be produced that would be stable indefinitely in that it would not evaporate. Examples of such reactive light-absorbing dye moieties include $X_m$- and $Y_n$-substituted dyes such as porphyrins, polyporphyrins and derivatives thereof, where $X_m$ and $Y_n$ are as defined above. A specific example comprises a porphyrin dye where X is hydroxy, Y is an acyl halide, and m and n are 4. The acyl halide-substituted porphyrins are dissolved in a non-aqueous phase such as chloroform, while the hydroxy-substituted porphyrins are dissolved in water. The two immiscible phases are contacted with one another to form a polyporphrin interfacial film. Films of strongly-absorbing dyes may also be formed by reacting other amine-substituted dyes such as Evans Blue or diamino-fluorescein, shown below, with acid chlorides such as trimesoyl chloride or fumaryl chloride.

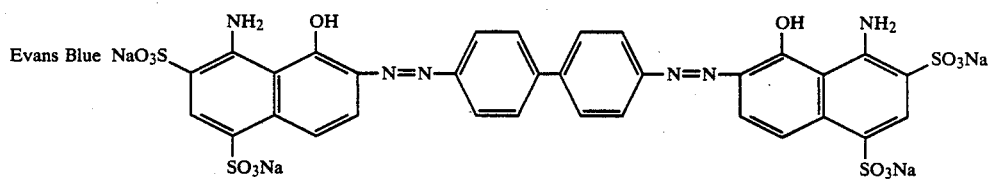

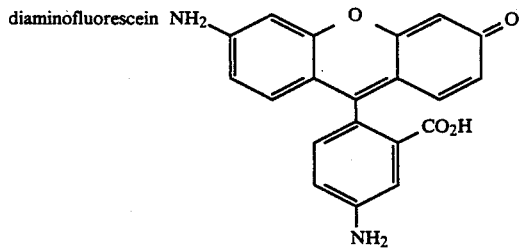

diaminofluorescein

The terms and expressions which have been employed in the foregoing specification are used therein as terms of description and not of limitation, and there is no intention, in the use of such terms and expressions, of excluding equivalents of the features shown and described or portions thereof, it being recognized that the scope of the invention is defined and limited only by the claims which follow.

What is claimed is:

1. A composition of matter comprising the thin film interfacial polymerization reaction product of $M_FX_m$ and $NY_n$ wherein $M_F$ is a moiety having chemical species-specific reversibly-complexing complexing sites, N is a moiety not having any chemical species-specific complexing sites, X and Y are groups that are mutually reactive in a condensation reaction, and m and n are integers $\geq 2$.

2. The composition of matter of claim 1 wherein X and Y are selected from acid halides, amines, aldehydes, alcohols, thiols, isocyanates and sulfonyl halides.

3. The composition of matter of claim 1 wherein $M_F$ is selected from organophosphoryl, cyclic crown ether, metalloporphyrin, metallo-Schiff base, metallophthalocyanine, macrocyclic metallobeta-diketone, pyrrolidone, metallocyclic ether, metallocyclic thioether, metallopolyazamacrocycle, and metallosulfonate.

4. The composition of matter of claim 3 wherein said metallo-Schiff base is selected from the structures

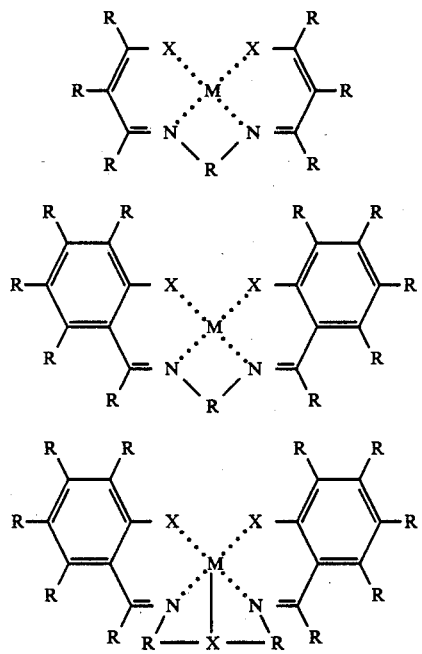

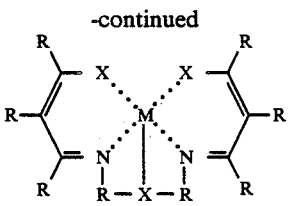

wherein M is a metal of +2 valence selected from cobalt, iron, copper, nickel, manganese, ruthenium and rhodium; X is

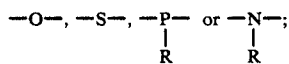

and R is hydrogen, alkyl, aryl, arylene halogen, alkoxy or a nitrogen-containing moiety.

5. The composition of matter of claim 3 wherein the metal of said metalloporphyrin, said metallo-Schiff base and said metallophthaloxcyanine is selected from cobalt (II) and iron (II).

6. The composition of matter of claim 5 comprising the interfacial polymerization reaction product of tetra-(aminophenyl)-porphyrin iron(II) and a polyacyl halide.

7. The composition of matter of claim 6 wherein the polyacyl halide is selected from fumaryl chloride and tetra-(carboxyphenyl acid chloride)porphyrin iron(II).

8. The composition of matter of claim 3 wherein said pyrrolidone is of the formula

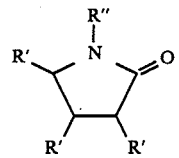

wherein R' is hydrogen, alkyl, aryl, cycloalkyl, substituted alkyl, substituted aryl, or substituted cycloalkyl; and R" is alkyl or substituted alkyl.

9. The composition of matter of claim 8 wherein said pyrrolidone is selected from N-methyl-2-pyrrolidone, N-cyclohexyl-2-pyrrolidone, 5-methyl-N-cyclohexyl-2-pyrrolidone, N-tallowalkyl-2-pyrrolidone, and N-cocoalkyl-2-pyrrolidone.

10. The composition of matter of claim 1 wherein $M_F$ is

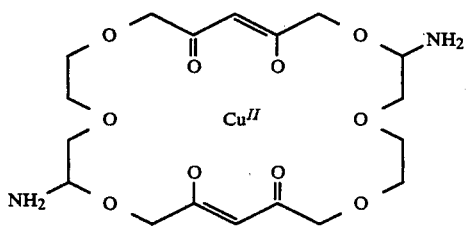

X is —NH$_2$; N is aryl; Y is —COHal or —NCO; m and n are 2 or 3; R is selected from hydrogen, alkyl and aryl; R' is a covalent bond or alkylene; Hal is halide.

11. The composition of matter of claim 1 wherein M$_F$ is dibenzo-18-crown-6; X is —NH$_2$; N is aryl; and Y is selected from acid halides and isocyanates.

12. The composition of matter of claim 11 wherein said acid halide is selected from isophthaloyl chloride, terephthaloyl chloride and trimesoyl chloride.

13. The composition of matter of claim 11 wherein said isocyanate is tolyldiisocyanate.

14. The composition of matter of claim 1, comprising the interfacial polymerization reaction product of
(a) a tetraazamacrocylic compound selected from the structures

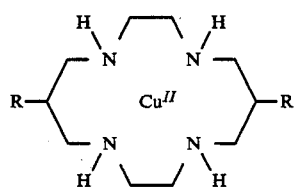

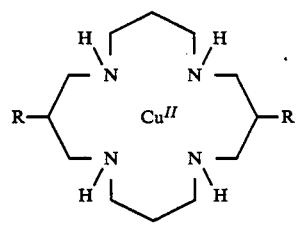

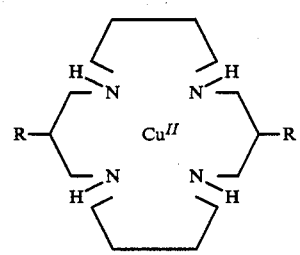

wherein R is hydrogen, alkyl containing from 1 to 20 carbon atoms, or aryl, and
(b) a polyacyl halide.

15. The composition of matter of claim 1 comprising the interfacial polymerization reaction product of a thioimino cryptand having the structure

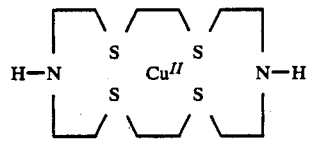

and a polyacyl halide.

16. The composition of matter of claim 7 comprising the interfacial polymerization reaction product of a diamino macrocylic acetylacetone copper (II) ligand having the structure

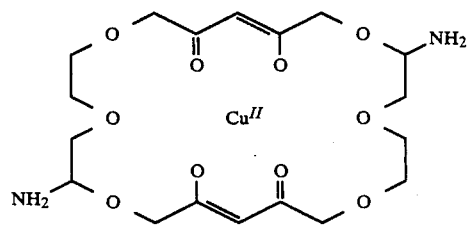

and a diacid halide.

17. The composition of matter of claim 1 comprising the metal ion sulfonate complex of the interfacial polymerization reaction product of tolyl diisocyanate sulfonate and a diol, said metal ion being selected from copper (I) and silver (I).

18. The composition of matter of claim 17 wherein said diol is diethylene glycol.

19. A composite selective membrane comprising a microporous support and the thin film interfacial polymerization reaction product of M$_F$X$_m$ and NY$_n$ wherein M$_F$ is a moiety having chemical species-specific reversibly-complexing complexing sites, N is a moiety not having any chemical species-specific complexing sites, X and Y are groups that are mutually reactive in a condensation reaction, and m and n are integers $\geq 2$.

20. The composite selective membrane of claim 19 wherein X and Y are selected from acid halides, amines, aldehydes, alcohols, thiols, isocyanates and sulfonyl halides.

21. The composite selective membrane of claim 19 wherein M$_F$ is selected from organophosphoryl, cyclic crown ether, metalloporphyrin, metallo-Schiff base, metallophthalocyanine, macrocyclic metallobeta-diketone, pyrrolidone, metallocyclic ether, metallocyclic thioether, metallopolyazamacrocycle, and metallosulfonate.

22. The composite selective membrane of claim 21 wherein said metallo-Schiff base is selected from the structures

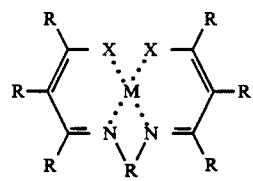

-continued

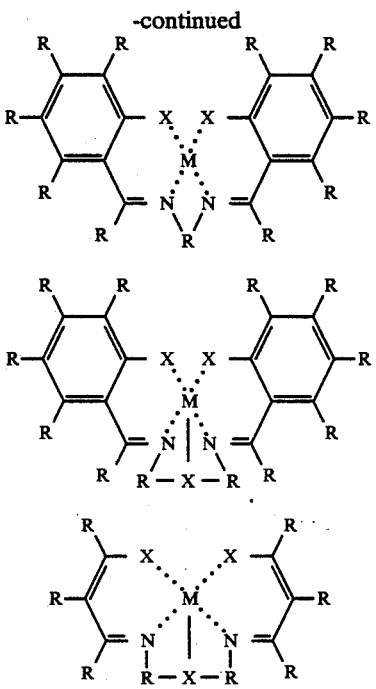

wherein M is a metal of +2 valence selected from cobalt, iron, copper, nickel, manganese, ruthenium and rhodium; X is

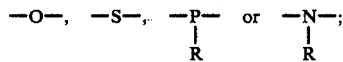

and R is hydrogen, alkyl, aryl, arylene halogen, alkoxy or a nitrogen-containing moiety.

23. The composite selective membrane of claim 21 wherein the metal of said metalloporphyrin, said metallo-Schiff base and said metallophthalocyanine is selected from cobalt(II) and iron(II).

24. The composite selective membrane of claim 23 comprising the interfacial polymerization reaction product of tetra-(aminophenyl)-porphyrin iron(II) and a polyacyl halide.

25. The composite selective membrane of claim 24 wherein the polyacyl halide is selected from fumaryl chloride and tetra-(carboxyphenyl acid chloride)-porphyrin iron(II).

26. The composite selective membrane of claim 21 wherein said pyrrolidone is of the formula

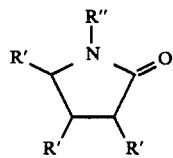

wherein R' is hydrogen or R''; R'' is aklyl, aryl, cycloalkyl, substituted alkyl, substituted aryl, or substituted cycloalkyl.

27. The composite selective membrane of claim 26 wherein said pyrrolidone is selected from N-methyl-2-pyrrolidone, N-cyclohexyl-2-pyrrolidone, 5-methyl-N-cyclohexyl-2-pyrrolidone, N-tallowalkyl-2-pyrrolidone, and N-cocoalkyl-2pyrrolidone.

28. The composite selective membrane of claim 19 wherein $M_F$ is

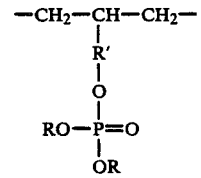

X is —NH$_2$; N is aryl; Y is —COHal or —NCO; m and n are 2 or 3; R is selected from hydrogen, alkyl and aryl; R' is a covalent bond or alkylene; and Hal is halide.

29. The composite selective membrane of claim 19 wherein $M_F$ is dibenzo-18-crown-6; X is —NH$_2$; N is aryl; and Y is selected from acid halides and isocyanates.

30. The composite selective membrane of claim 29 wherein said acid halide is selected from isophthaloyl chloride, terephthaloyl chloride and trimesoyl chloride.

31. The composite selective membrane of claim 29 wherein said isocyanate is tolyldiisocyanate.

32. The composite selective membrane of claim 19 wherein
(a) $M_FX_m$ is a tetraazamacrocylic compound selected from the structures

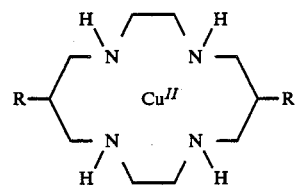

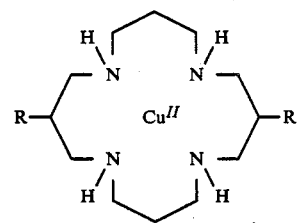

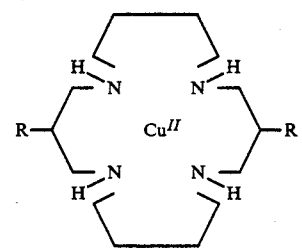

wherein R is hydrogen, alkyl containing from 1 to 20 carbon atoms, or aryl, and
(b) $NY_n$ is a polyacyl halide.

33. The composite selective membrane of claim 19 wherein $M_FX_m$ is a thioimino cryptand having the structure and NY$_n$ is a polyacyl halide.

34. The composite selective membrane of claim 19 wherein M$_F$X$_m$ is a diamino macrocylic acetylacetone copper(II) ligand having the structure

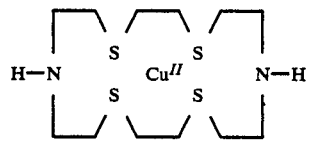

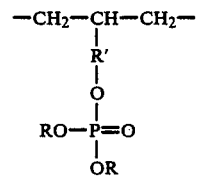

and NY$_n$ is a polyacyl halide.

35. The composite selective membrane of claim 19 wherein said thin film interfacial polymerization reaction product is of tolyl diisocyanate sulfonate and a diol, said metal ion being selected from copper (I) and silver (I).

36. The composite selective membrane of claim 35 wherein said diol is ethylene glycol.

* * * * *